United States Patent
McKeown et al.

(10) Patent No.: US 12,311,304 B2
(45) Date of Patent: May 27, 2025

(54) DEVICE FOR DECONTAMINATING A REGION AND VERIFYING DECONTAMINATION OF THE REGION

(71) Applicant: EAGLE AEROSPACE, LTD., Campbellford (CA)

(72) Inventors: Samuel William McKeown, Campbellford (CA); Stephen Lyle McKeown, Campbellford (CA); Benjamin Francis McKeown, Campbellford (CA); Joseph Stephen McKeown, Campbellford (CA); Trevor Harley, Marmora (CA)

(73) Assignee: EAGLE AEROSPACE LTD., Campbellford (CA)

( * ) Notice: Subject to any disclaimer, the term of this patent is extended or adjusted under 35 U.S.C. 154(b) by 504 days.

(21) Appl. No.: 17/533,345

(22) Filed: Nov. 23, 2021

(65) Prior Publication Data

US 2022/0161175 A1   May 26, 2022

Related U.S. Application Data

(60) Provisional application No. 63/117,716, filed on Nov. 24, 2020.

(51) Int. Cl.
*B01D 46/00* (2022.01)
*A61L 9/20* (2006.01)
(Continued)

(52) U.S. Cl.
CPC ............ *B01D 46/0028* (2013.01); *A61L 9/20* (2013.01); *B01D 46/0005* (2013.01);
(Continued)

(58) Field of Classification Search
CPC ............ B01D 46/0028; B01D 46/0005; B01D 46/0043; B01D 46/4245; B01D 46/442;
(Continued)

(56) References Cited

U.S. PATENT DOCUMENTS

| 5,360,722 A | 11/1994 | Inoue et al. |
| 6,514,721 B2 | 2/2003 | Spurrell |

(Continued)

FOREIGN PATENT DOCUMENTS

| DE | 102020120046 A1 * | 10/2020 |
| EP | 0 138 664 A2 | 4/1985 |

(Continued)

OTHER PUBLICATIONS

Machine translation of DE-102020120046-A1 (Year: 2020).*
(Continued)

*Primary Examiner* — Robert Clemente
(74) *Attorney, Agent, or Firm* — Wentsler LLC

(57) ABSTRACT

A self contained, 1 V to 550 V powered UVC device used to sterilize spaces like vehicle cabins or indoor rooms or spaces, while providing the ability to monitor both pre and post sterilization. While operating, the device would collect, on suitable gathering/testing media, both air that has been sterilized, and unsterilized air that passes through the media, allowing the media to be tested for the presence of both active pathogens that have not yet been killed from the device, as well as killed pathogens in the sterilized area. The UVC and media components may be integrated into one unit, or be powered and used both in combination, or as separate devices performing the sterilization and the sampling media. At the termination of UVC sterilization, additional different media has the now sterilized cabin or room air circulated through it, and with further media testing and (Continued)

evaluation, the efficiency/effectiveness of the sterilization process can be audited, and system operators can be advised.

8 Claims, 5 Drawing Sheets

(51) Int. Cl.
    *B01D 46/42*     (2006.01)
    *B01D 46/44*     (2006.01)
    *B01D 46/54*     (2006.01)

(52) U.S. Cl.
    CPC ..... *B01D 46/0043* (2013.01); *B01D 46/4245* (2013.01); *B01D 46/442* (2013.01); *B01D 46/543* (2013.01); *A61L 2209/11* (2013.01); *B01D 2273/30* (2013.01); *B01D 2279/65* (2013.01)

(58) Field of Classification Search
    CPC ... B01D 2273/30; B01D 2279/65; A61L 9/20; A61L 2209/11
    See application file for complete search history.

(56) References Cited

U.S. PATENT DOCUMENTS

| | | | |
|---|---|---|---|
| 6,565,638 B1 | 5/2003 | Sugita et al. | |
| 6,777,228 B2 | 8/2004 | Lejeune | |
| 7,405,073 B2 | 7/2008 | Tilles et al. | |
| 7,857,957 B2 | 12/2010 | Cheng et al. | |
| 8,828,714 B2 | 9/2014 | Nishikawa et al. | |
| 9,433,883 B2 | 9/2016 | Takenaka et al. | |
| 9,631,222 B2 | 4/2017 | Ketcham et al. | |
| 9,689,792 B1 | 7/2017 | Sickenberger et al. | |
| 9,989,445 B2 | 6/2018 | Ligugnana et al. | |
| 10,018,537 B2 | 7/2018 | Verdier et al. | |
| 10,371,616 B2 | 8/2019 | Park et al. | |
| 10,392,648 B2 | 8/2019 | Park et al. | |
| 10,732,081 B2 | 8/2020 | Kocher et al. | |
| 2004/0120845 A1 | 6/2004 | Potember et al. | |
| 2005/0136507 A1 | 6/2005 | Sullivan et al. | |
| 2006/0257853 A1 | 11/2006 | Herman | |
| 2016/0002700 A1 | 1/2016 | Ketcham et al. | |
| 2016/0025603 A1 | 1/2016 | Kindt et al. | |
| 2016/0116404 A1 | 4/2016 | Bertaux | |
| 2017/0321877 A1 | 11/2017 | Polidoro | |
| 2018/0193843 A1 | 7/2018 | Jacobs et al. | |
| 2018/0306679 A1 | 10/2018 | Sobek | |
| 2019/0212232 A1 | 7/2019 | Hwang et al. | |
| 2019/0360686 A1 | 11/2019 | Pendo et al. | |
| 2020/0009286 A1 | 1/2020 | Zarcone et al. | |
| 2020/0110008 A1 | 4/2020 | Park et al. | |
| 2020/0116691 A1 | 4/2020 | Maffei et al. | |

FOREIGN PATENT DOCUMENTS

| | | | | |
|---|---|---|---|---|
| GB | 2215234 A | * | 9/1989 | ............... A61L 9/16 |
| JP | 2004-159508 A | | 6/2004 | |
| JP | 5729713 B2 | | 6/2015 | |
| WO | 90/14437 A1 | | 11/1990 | |
| WO | 2011/107874 A1 | | 9/2011 | |
| WO | 2019/195217 A1 | | 10/2019 | |

OTHER PUBLICATIONS

International Search Report for corresponding International Application No. PCT/CA2021/051662 mailed Feb. 24, 2022.
Miller et al., "Evaluation of a Methodology for Quantifying the Effect of Room Air Ultraviolet Germicidal Irradiation on Airborne Bacteria", Aerosol Science & Technology, Nov. 30, 2010, 33:3, pp. 274-295.
Lin et al., "Pulsed Ultraviolet Light Decontamination of Virus-laden Airstreams", Aerosol Science & Technology, 2017, vol. 51, No. 5, pp. 554-563.
Brosseau et al., "Investigate and Identify Means of Controlling Virus in Indoor Air by Ventilation, Filtration or Source Removal", 776-RP, Jan. 26, 1994, pp. 1-115; https://www.ashrae.org/file%20library/technical%20resources/covid-19/rp776.pdf.
"Guidelines for Environmental Infection Control in Health-Care Facilities", 2003, CDC, https://www.cdc.gov/infectioncontrol/guidelines/environmental/background/sampling.htm (downloaded Jan. 12, 2022).

* cited by examiner

DEVICE FOR DECONTAMINATING A REGION AND VERIFYING DECONTAMINATION OF THE REGION

CROSS-REFERENCE TO RELATED APPLICATIONS

This application claims priority to, and any other benefit of U.S. Provisional Application Ser. No. 63/117,716, filed Nov. 24, 2020, the entire disclosure of which is incorporated herein by reference as though recited herein in its entirety.

FIELD

The present invention relates to a system for treating a region and detecting contaminates in that region, in particular, viruses, bacteria, etc. in a small enclosed area, e.g., an airplane cabin.

BACKGROUND

Recently, the spread of contagious viruses, e.g., COVID-19, has resulted in a large decline in passenger travel in most transportation modes, e.g., buses, planes, trains, etc. Most passengers are concerned with being exposed to contagious viruses while traveling in these transportation vehicles. Without familiarity with other passengers it is difficult to know if one has been exposed to the contagious virus.

The present invention provides a system and/or method that may quickly and efficiently decontaminate a transportation vehicle after passengers have exited and verify that the vehicle has indeed been decontaminated before new passengers enter the vehicle.

BRIEF SUMMARY

There is provided an assembly for treating and detecting contaminates in a region. The assembly includes a housing defining an internal volume and an opening providing fluid communication between the region and the internal volume. An ultraviolet light is attached to the housing and is configured to irradiate the region with ultraviolet C (UVC) light to kill the contaminates in the region. A first body is attachable to the housing and includes an internal cavity and an inlet opening extending through a wall of the first body. The inlet opening extends through a wall of the first body and provides fluid communication between the region and the internal cavity. A fan is disposed in the first body for drawing air from the region into the internal cavity through the inlet opening. A filter membrane is disposed proximate the opening and is configured to remove contaminates from the air drawn into the internal cavity through the opening.

In accordance with another aspect, the housing includes a fan configured to draw air from the region into the housing through the opening of the housing. The housing also includes a filter membrane disposed proximate the opening of the housing configured to remove contaminates from the air drawn into the housing.

In accordance with another aspect, the housing includes a holder attached to a wall of the housing for removably receiving the filter membrane of the housing therein.

In accordance with another aspect, the housing includes opposing ends, and the fan of the housing is disposed at one of the opposing ends. The fan of the housing is operable to draw the air into the housing.

In accordance with another aspect, the first body is removably attachable to the housing.

In accordance with another aspect, the first body includes a power cable attachable to the housing for supplying power from the housing to the fan of the first body.

In accordance with another aspect, the first body includes a battery for supplying power to the fan of the first body.

In accordance with another aspect, the assembly also includes a second body attachable to the housing. The second body includes an internal cavity and an inlet opening extending through a wall of the second body for providing fluid communication between the region and the internal cavity. A fan is disposed in the internal cavity of the second body for drawing air from the region into the internal cavity through the opening. A filter membrane is disposed proximate the opening of the second body and is configured to remove contaminates from the air drawn into the internal cavity through the opening of the second body.

In accordance with another aspect, the assembly also includes a control unit including logic to activate the ultraviolet light and activate the fan in the first body.

In accordance with yet another aspect, there is provided a collection device for removing contaminates from a region. The collection device includes a body with an internal cavity and an inlet opening extending through a wall of the body. The inlet opening provides fluid communication between the region and the internal cavity. An outlet opening extends through another wall of the body for providing fluid communication between the region and the internal cavity. The body also includes a fan disposed in the body for generating an air stream the flows from the region, into the inlet opening, through the internal cavity, and through the outlet opening and back to the region. A filter membrane is disposed in the air stream for removing contaminates from the air stream.

In accordance with another aspect, the body defines a slot dimensioned to removably receive the filter membrane therethrough.

In accordance with another aspect, the body includes an attachment element for removably attaching the body to a surface.

In accordance with another aspect, the collection device also includes a battery for supplying power to the fan of the body.

In accordance with another aspect, the inlet opening and the outlet opening are formed through in opposing walls of the body.

In accordance with another aspect, the collection device also includes a power cable for supplying power from a power source to the fan of the body.

In accordance with yet another aspect, a method for treating and detecting contaminates in an area includes irradiating the area with UVC light from an ultraviolet light disposed in a first housing, and simultaneously drawing air through a filter membrane disposed in the first housing to capture contaminates thereon during a first time period. The method also includes drawing air through a second filter membrane disposed in a second housing during a second time period after the first time period, and thereafter analyzing the second filter membrane to determine a level of contaminates remaining in the area after the first time period.

In accordance with another aspect, wherein the air is drawn through the second filter membrane via a fan disposed in the second housing.

In accordance with another aspect, the method also includes drawing air through a third filter membrane before the first time period, and analyzing the third filter membrane to determine an initial level of contaminates in the area.

In accordance with another aspect, wherein the filter membrane disposed in the second housing has a size of 0.001 to 10 microns.

In accordance with another aspect, wherein the filter membrane disposed in the first housing has a size that is less than or equal to 0.3 microns.

DETAILED DESCRIPTION

Figure 1:
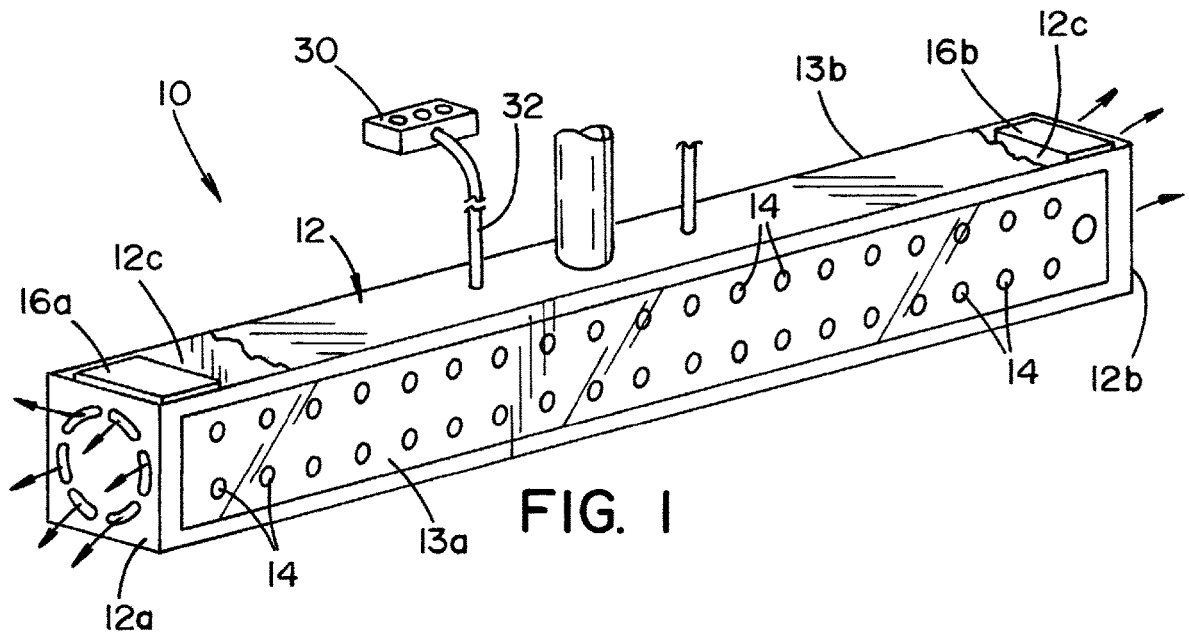
FIG. 1 is a front perspective view of a device for decontaminating an enclosed region, according to one embodiment of the present invention.

Referring to FIG. 1, a device 10 for decontaminating an enclosed region is shown. The device 10 includes an elongated housing 12 having a first end 12a and a second end 12b. The housing 12 defines an internal volume 12c therein that is configured to receive a plurality of ultraviolet (UV) lights 14. The UV lights 14 are configured to emit UV light in the range of 200 nm to 280 nm, preferably at 275 nm (referred to as "UVC light"). In particular, the UVC light emitted by the UV lights 14 is selected to be at an intensity and wavelength to kill viruses, bacteria, etc. when exposed for a predetermined period of time. It is contemplated that the UVC light may eliminate up to 99.999% of viruses once the energy level emitted reaches 22 mj/cm$^2$. It is also contemplated that the UVC light emitted by the UV lights 14 may be configured to reach 25 mj/cm$^2$, at a minimum.

As illustrated, the UV lights 14 are on a front face 13a of the housing 12. In the embodiment shown, the UV lights 14 are disposed in two horizontal rows. It is contemplated that the UV lights 14 may be disposed in any other arrangement so long as the UV lights 14 effectively irradiate an enclosed region (not shown).

Disposed at each end 12a, 12b of the housing 12 is a fan 16a, 16b, respectively. The fans 16a, 16b are configured to draw air into the housing 12 through an opening 18 (FIG. 3) on a rear face 13b of the housing 12. The air drawn into the housing 12 by the fans 16a, 16b is passed over the UV lights 14 to help maintain the device 10 below a maximum temperature during operation of the device 10. In the embodiment shown, the opening 18 is formed by a plurality of elongated openings 18a. It is contemplated that the opening 18 may be a single opening.

Figure 2:
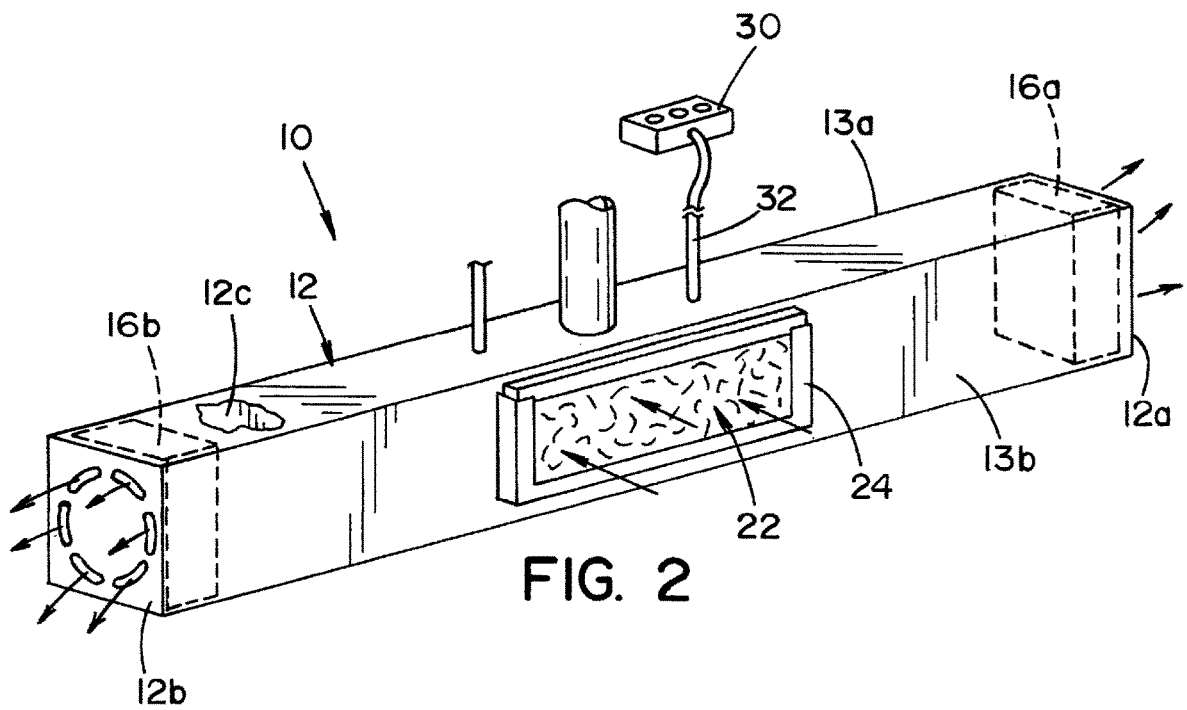
FIG. 2 is a rear perspective view of the device of FIG. 1, including a filter membrane disposed over an inlet of the device.
Figure 3:
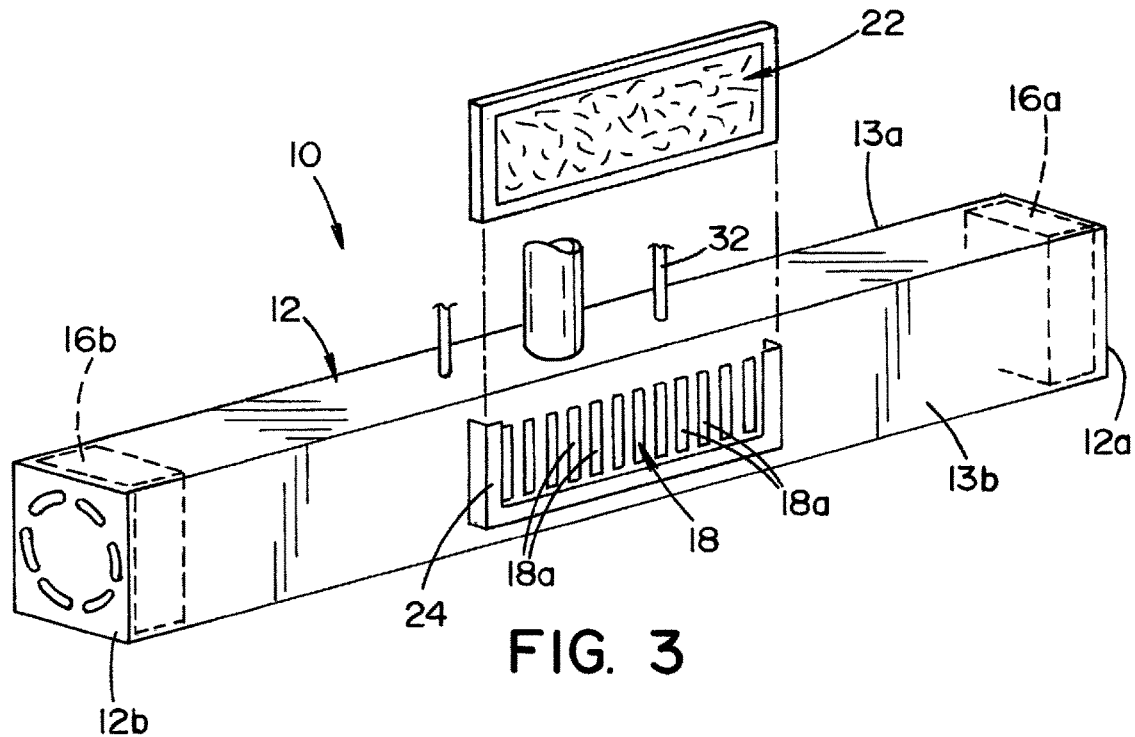
FIG. 3 is an exploded view of the device of FIG. 2.

Referring to FIGS. 2 and 3, a filter membrane 22 may be disposed over the opening 18 on the rear face 13b of the housing 12. The housing 12 may include a holder 24 that is configured to retain the filter membrane 22 over the opening 18. The filter membrane 22 is sized to capture viruses, bacteria, etc. that are drawn into the housing 12. It is contemplated that the filter membrane may have a size of 0.3 microns or less to effectively capture viruses, bacteria, etc. without appreciably dimensioning the flow of air into the housing 12 during operation.

Figure 4:
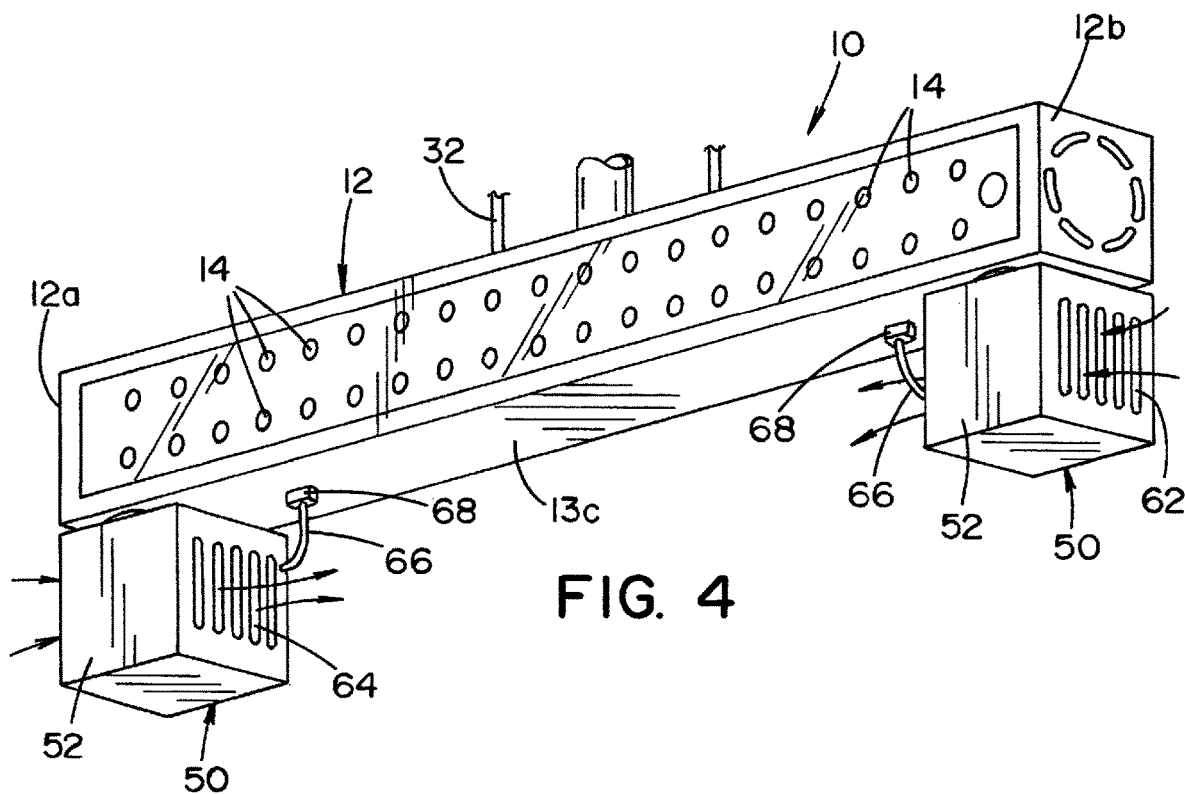
FIG. 4 is a bottom perspective view of a device for decontaminating an enclosed region, according to another embodiment of the present invention.
Figure 5:
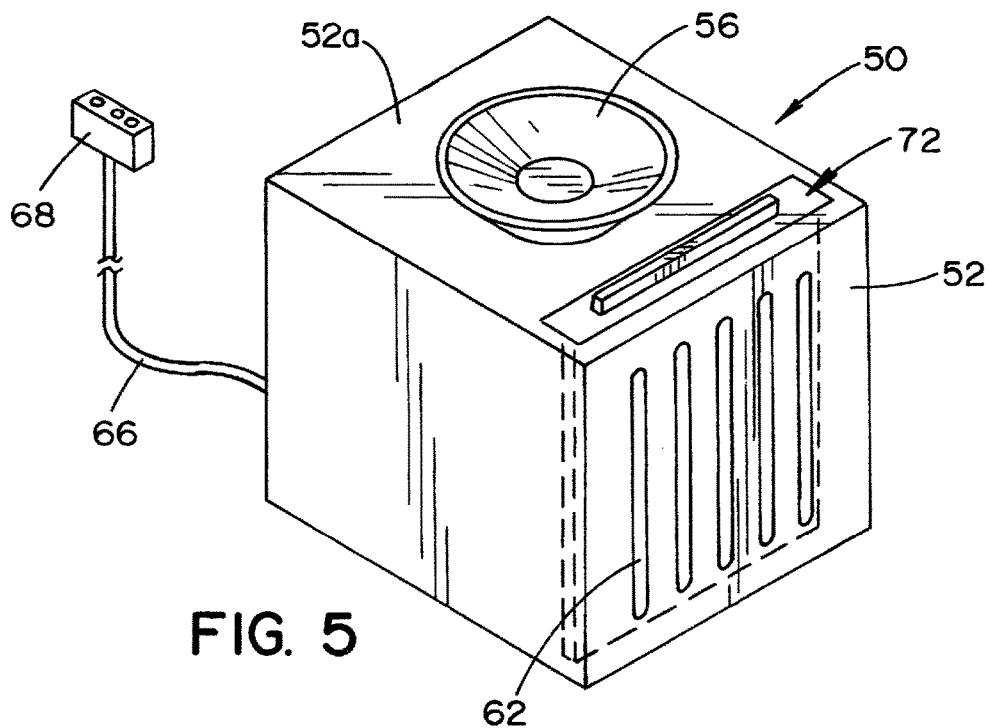
FIG. 5 is a front perspective view of a collection cube for use on the device of FIG. 4.
Figure 6:
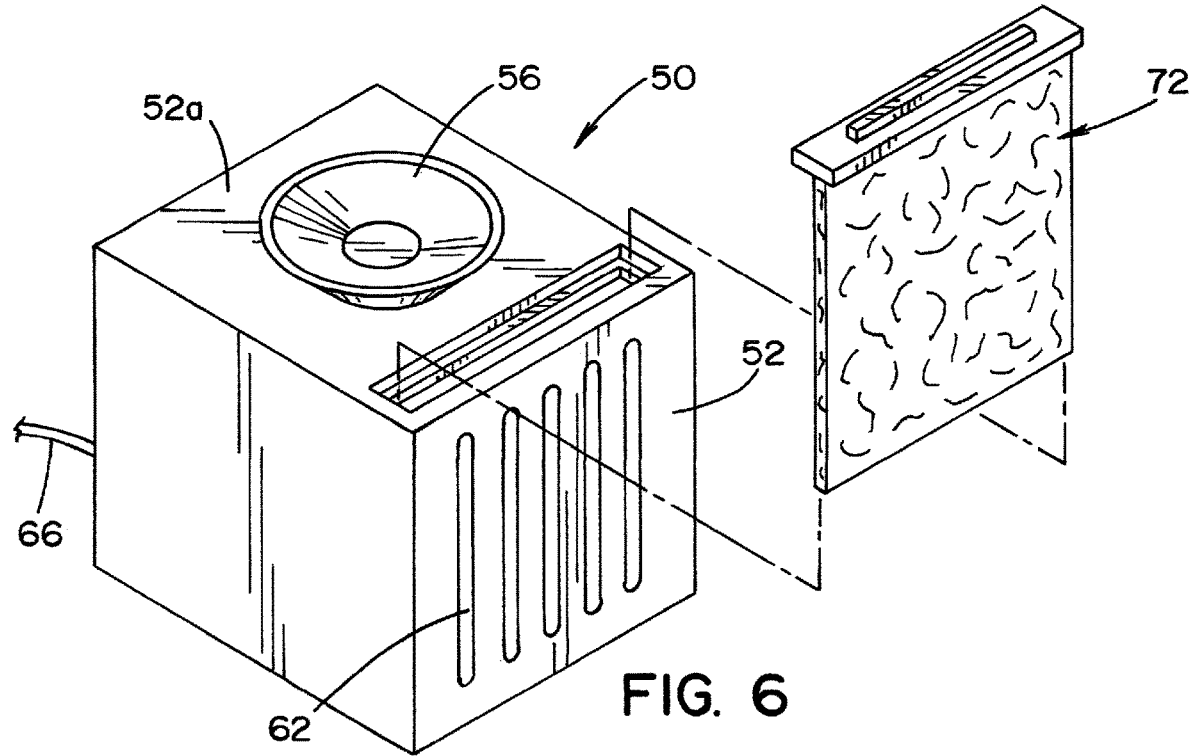
FIG. 6 is an exploded view of the collection cube of FIG. 5, illustrating a filter membrane removed from the collection cube.
Figure 7:
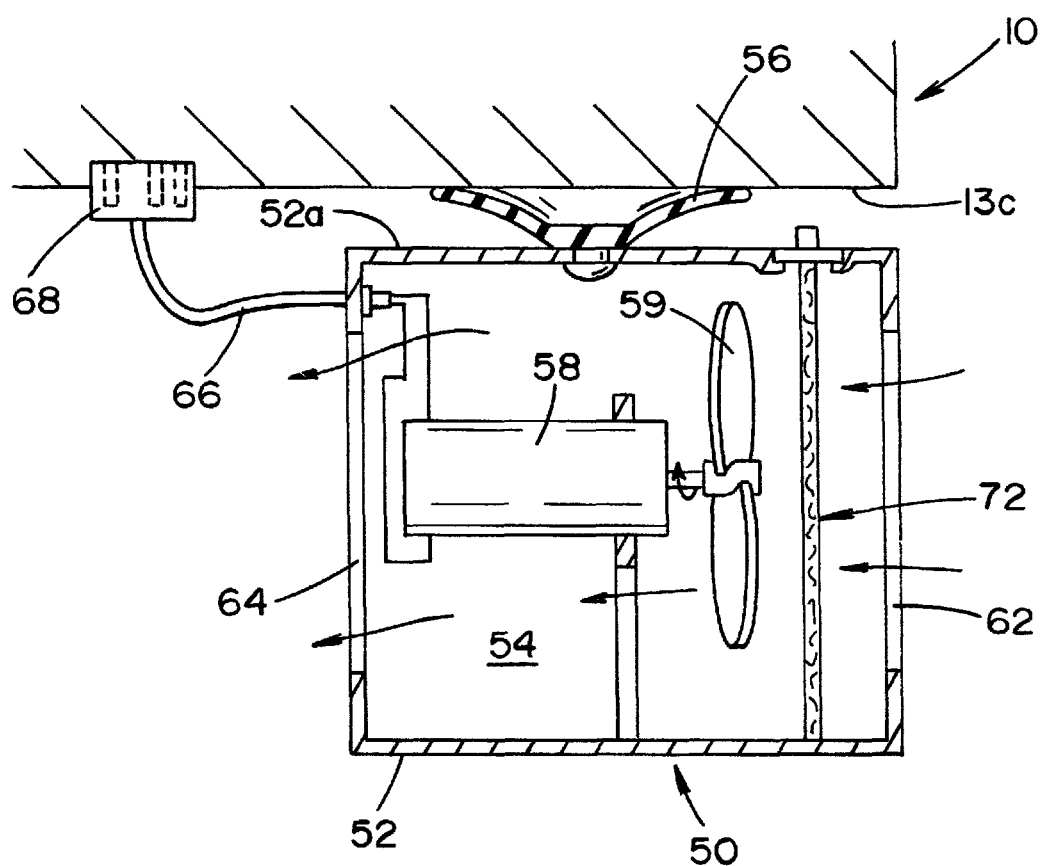
FIG. 7 is a partial section view taken from FIG. 4 illustrating the collection cube attached to a bottom surface of the device.

Referring to FIG. 4, a pair of collection cubes 50 are illustrated attached to the bottom face 13c of the housing 12. Referring to FIGS. 5-7, the collection cube 50 is shown. The collection cube 50 includes a body 52 that defines an internal volume 54 (FIG. 7) of the collection cube 50. An attachment element 56 is attached to a top surface 52a of the body 52 for securing the collection cube 50 to the housing 12. The attachment element 56 is illustrated as a suction cup. It is contemplated that the attachment element 56 may be any other type of structure that temporarily secures the collection cube 50 to the housing 12, including, but not limited to, fasteners, clips, a key/groove arrangement, adhesive, etc.

A fan motor 58 and fan 59 are disposed within the internal volume 54. The fan 59 is configured to draw air into the internal volume 54 through a first opening 62 of the body 52 and exhaust the air through a second opening 64. It is contemplated that the fan motor 58 may be reversible such that air can be drawn in by the fan 59 through the second opening 64 and exhausted out through the first opening 62. A power cable 66 is provided for attaching the fan motor 58 to the housing 12 using a connector 68.

A removable membrane 72 is configured to be disposed within the internal volume 54. The removable membrane 72 may be sized to capture viruses, bacteria, etc. thereon on. In this respect, the removable membrane 72 may be 0.001 to 10 microns.

Referring back to FIG. 4, the collection cube 50 may be secured to the housing 12 such that one collection cube 50 is located at each end of the housing 12. The power cable 66 for each collection cube 50 includes a connector 68 for connecting to a mating connector (not shown) on the housing 12.

A control unit 30 (FIGS. 1 and 2) may be provided internally, or externally, or a hybrid thereof for controlling the operation of the device 10. The control unit 30 may be a conventional computer unit that includes a central processing unit (CPU) that processes commands and input and generates output commands, an input unit for receiving commands from the user and signals from various components of the device 10, an output unit for conveying commands from the CPU to the various components of the device 10 and a storage unit for storing data received and/or generated by the CPU. Various control lines, e.g., control cable 32, may extend from the control unit 30 to the components of the device 10. It is contemplated that the control lines may be configured to send power and/or signals between the respective component and the control unit 30. It is also contemplated that the control lines may represent other commonly known types of wired and/or wireless communication between the control unit 30 and the various components of the device 10, or external devices or systems including but not limited to, hard wire, Wi-Fi, Ethernet, Bluetooth, etc. and combinations thereof.

It is contemplated that the device 10 may be connected to a power supply (not shown) that supplies a voltage of between about 1 V and 550 V to the device 10 and/or the collection cube 150.

Figure 8:
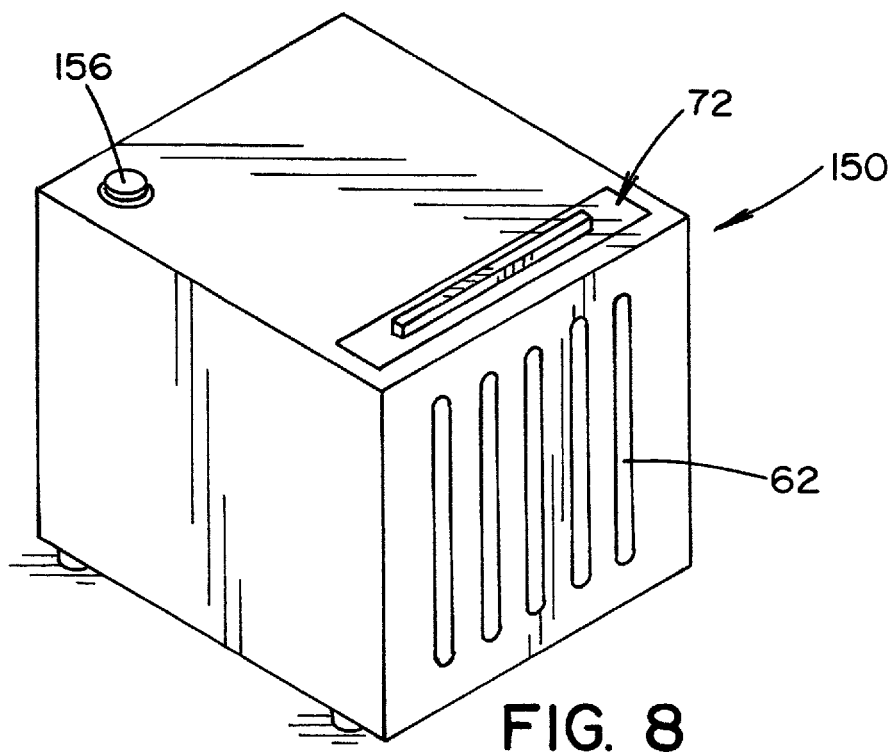
FIG. 8 is a front perspective view of a collection cube, according to another embodiment.
Figure 9:
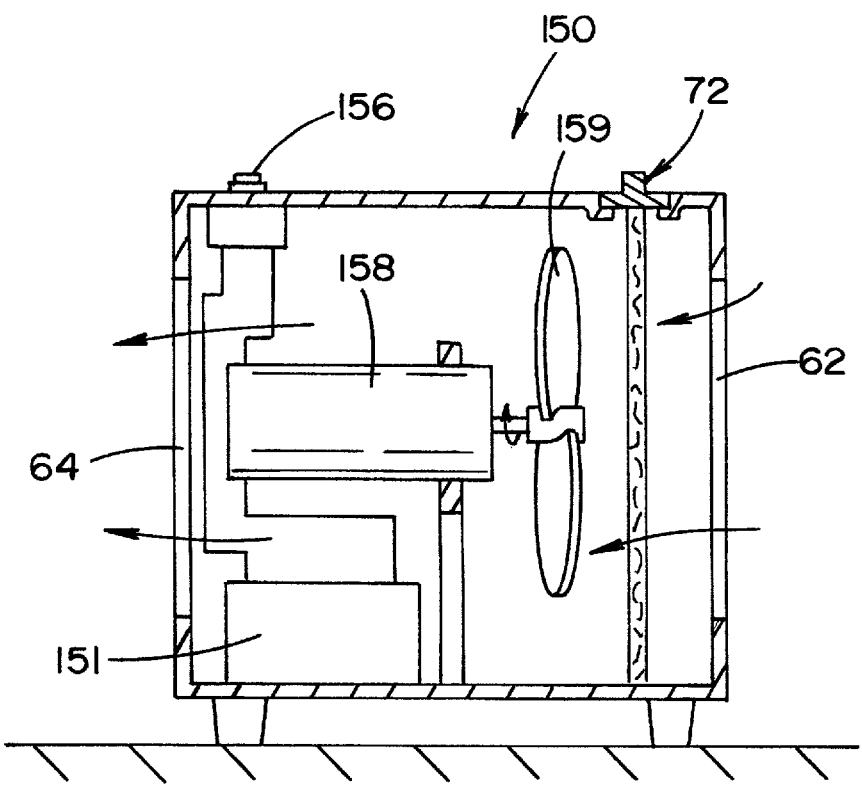
FIG. 9 is a section view taken from FIG. 8 of the collection cube.

Referring to FIGS. 8 and 9, another embodiment of a collection cube 150 is illustrated. In this embodiment, the collection cube 152 is a stand-alone unit that may be mounted in any location within an enclosed area. The collection cube 152 may include a battery 151 for supplying power to a fan motor 158 that drives a fan 159. As illustrated, the collection cube 152 includes a button 156 for allowing a user to energize the fan motor 158 as desired. It is also contemplated that the collection cube may be connected to the control unit 30 using commonly known types of wired and/or wireless communication between the control unit 30 and the collection cube 150, including but not limited to, hard wire, Wi-Fi, Ethernet, Bluetooth, etc. and combinations thereof. In this manner, the collection cube 150 may be remotely operated by a user or the control unit 30, as desired. It is also contemplated that instead of the battery 154, a power cable (not shown) may connect the collection cube 150 to a power supply.

During operation, the device 10 is placed within an enclosed area (not shown). The device 10 typically would be placed in the enclosed area after the occupants have exited. Once the enclosed area is free of occupants, the device 10 may be energized to start a decontamination phase. In particular, the UV lights 14 may be energized to expose the contents of the enclosed area to UVC radiation at a desired dosage to decontaminate the enclosed area. It is contemplated that the fans 16a, 16b may be energized to convey air through the housing 12 of the device 10 to maintain the device 10 below a maximum temperature. As the fans 16a, 16b convey air through the housing 12, contaminants in the enclosed area may be collected on filter membrane 22. The fans 16a, 16b also add in circulating air within the enclosed area so that the air may be properly sterilized by the light emitted by the UV lights 14.

It is contemplated that the user may initiate the decontamination phase by selecting from a pre-set time interval for a given enclosed area, e.g., different sized vehicles, or airplane cabins, in order to ensure that the UVC dosage is sufficient to decontaminate the enclosed area. A timer in the device 10 may then count down until the decontamination phase is complete.

Once the decontamination phase is completed (as determined by reaching the desired dosage of UV radiation to decontaminate the enclosed area), the control unit 30 may initiate a collection phase by energizing one or more collection cubes 50, 150 to draw air into the internal volume 54 of the collection cube 50, 150. As air passes through the collection cube 50, 150, decontaminate in the enclosed area may be collected on the removable membrane 72. It is contemplated that the fan motors 58, 158 may be energized for a sufficient amount of time to properly sample the air in the enclosed area. Once the collection phase is completed, a user may detach the collection cube 50 from the housing 12 or remove the collection cube 150 from the enclosed area.

The collection cube 50, 150 and/or the filter membrane 22 may then be taken in a safety sealed pouch or similar to a lab or test area for analysis. Once in the lab, an operator may test the removable membrane 72 from the collection cube 50, 150 in a sterile environment, e.g., in a laboratory exhaust hood. It is also contemplated that the fan motors 58, 158 may be run in reverse so that any contaminate on the removable membrane 72 may be blown off and collected in a suitable collection device. Once a proper sampling of the filter membrane 22 and the removable membrane(s) 72 is completed, an analysis may be performed to determine if any active contaminates remained in the enclosed area after the decontamination cycle.

It is also contemplated that one of the collection cubes 50, 150 may be activated prior to the decontamination phase such that the collection cube 50, 150 samples air that has not yet been sterilized by the device 10. During a subsequent collection phase this collection cube 50, 150 would not be active so as to not re-contaminate the enclosed area. In this respect, the efficiency/effectiveness of the device 10 can be audited and the user notified if the device 10 is not operating within desired limits, or, if an area that has been treated by the device 10 is contaminated.

The present invention thus provides a system for decontaminating an enclosed area and for sampling the air in the enclosed area to verify proper operation of the system, the presence of deactivated contaminate, or the presence of active contaminate.

The invention has been described with reference to the example embodiments described above. Modifications and alterations will occur to others upon a reading and understanding of this specification. Examples embodiments incorporating one or more aspects of the invention are intended to include all such modifications and alterations insofar as they come within the scope of the appended claims and their equivalents.

What is claimed is:

1. An assembly for treating and detecting contaminates in a region, the assembly comprising:

a housing defining an internal volume and an opening providing fluid communication between the region and the internal volume, wherein the housing comprises opposing ends and a fan of the housing is disposed at one of the opposing ends and is operable to draw air into the housing through the opening of the housing;

an ultraviolet light attached to the housing and configured to irradiate the region with UVC light to kill the contaminates in the region; and a first body attachable to the housing, wherein the first body includes:

an internal cavity, an inlet opening extending through a wall of the first body for providing fluid communication between the region and the internal cavity, a fan disposed in the first body for drawing air from the region into the internal cavity through the inlet opening, and a filter membrane disposed proximate the inlet opening and configured to remove contaminates from the air drawn into the internal cavity through the inlet opening.

2. The assembly according to claim 1, wherein the housing comprises:

a filter membrane disposed proximate the opening of the housing and configured to remove contaminates from the air drawn into the housing.

3. The assembly according to claim 2, wherein the housing further comprises a holder attached to a wall of the housing for removably receiving the filter membrane of the housing therein.

4. The assembly according to claim 1, wherein the first body comprises a power cable attachable to the housing for supplying power from the housing to the fan of the first body.

5. The assembly according to claim 1, wherein the first body comprises a battery for supplying power to the fan of the first body.

6. The assembly according to claim 1, wherein the assembly further comprises
- a second body attachable to the housing, wherein the second body includes:
  - an internal cavity,
  - an inlet opening extending through a wall of the second body for providing fluid communication between the region and the internal cavity,
  - a fan disposed in the internal cavity of the second body for drawing air from the region into the internal cavity through the opening, and
  - a filter membrane disposed proximate the inlet opening of the second body and configured to remove contaminates from the air drawn into the internal cavity through the inlet opening.

7. The assembly according to claim 1, wherein the assembly further comprises a control unit comprising logic to:
- activate the ultraviolet light; and
- activate the fan in the first body.

8. An assembly for treating and detecting contaminates in a region, the assembly comprising:
- a housing defining an internal volume and an opening providing fluid communication between the region and the internal volume;
- an ultraviolet light attached to the housing and configured to irradiate the region with UVC light to kill the contaminates in the region; and
- a first body attachable to the housing, wherein the first body includes:
  - an internal cavity,
  - an inlet opening extending through a wall of the first body for providing fluid communication between the region and the internal cavity,
  - a fan disposed in the first body for drawing air from the region into the internal cavity through the inlet opening, and
  - a filter membrane disposed proximate the inlet opening and configured to remove contaminates from the air drawn into the internal cavity through the inlet opening,
  - wherein the first body is removably attachable to the housing.

* * * * *